US010137197B2

(12) United States Patent
Bolli et al.

(10) Patent No.: US 10,137,197 B2
(45) Date of Patent: *Nov. 27, 2018

(54) PROCESS FOR PREPARING AN IMMUNOGLOBULIN PREPARATION

(71) Applicant: CSL Behring AG, Bern (CH)

(72) Inventors: Reinhard Franz Bolli, Guemligen (CH); Werner Maeder, Oftringen (CH); Peter Lerch, Bern (CH)

(73) Assignee: CSL Behring AG, Bern (CH)

( * ) Notice: Subject to any disclaimer, the term of this patent is extended or adjusted under 35 U.S.C. 154(b) by 154 days.

This patent is subject to a terminal disclaimer.

(21) Appl. No.: 14/970,326

(22) Filed: Dec. 15, 2015

(65) Prior Publication Data

US 2016/0151495 A1 Jun. 2, 2016

Related U.S. Application Data

(63) Continuation of application No. 13/577,220, filed as application No. PCT/EP2011/051556 on Feb. 3, 2011, now Pat. No. 9,241,897.

(30) Foreign Application Priority Data

Feb. 4, 2010 (EP) ..................................... 10001164

(51) Int. Cl.
| A61K 47/22 | (2006.01) |
| A61K 9/00 | (2006.01) |
| A61K 47/18 | (2017.01) |
| C07K 16/00 | (2006.01) |
| A61K 39/395 | (2006.01) |

(52) U.S. Cl.
CPC ............ *A61K 47/22* (2013.01); *A61K 9/0019* (2013.01); *A61K 39/395* (2013.01); *A61K 47/183* (2013.01); *C07K 16/00* (2013.01)

(58) Field of Classification Search
None
See application file for complete search history.

(56) References Cited

U.S. PATENT DOCUMENTS

| 4,186,192 A | 1/1980 | Lundblad et al. |
| 4,360,451 A | 11/1982 | Schmolka |
| 4,362,661 A | 12/1982 | Ono et al. |
| 4,396,608 A | 8/1983 | Tenold |
| 4,439,421 A | 3/1984 | Hooper et al. |
| 4,499,073 A | 2/1985 | Tenold |
| 4,849,508 A | 7/1989 | Magnin et al. |
| 4,880,913 A | 11/1989 | Doleschel et al. |
| 5,164,487 A | 11/1992 | Kothe et al. |
| 5,177,194 A | 1/1993 | Sarno et al. |
| 5,503,827 A | 4/1996 | Woog et al. |
| 5,593,675 A | 1/1997 | Hodler et al. |
| 5,871,736 A | 2/1999 | Bruegger et al. |
| 5,945,098 A | 8/1999 | Sarno et al. |
| 6,069,236 A | 5/2000 | Burnouf-Radosevich et al. |
| 6,093,324 A | 7/2000 | Bertolini et al. |
| 6,162,904 A | 12/2000 | Mamidi et al. |
| 6,171,586 B1 | 1/2001 | Lam et al. |
| 6,252,055 B1 | 6/2001 | Relton |
| 6,303,113 B1 | 10/2001 | Woog et al. |
| 8,715,652 B2 | 5/2014 | Bolli et al. |
| 9,241,897 B2 * | 1/2016 | Bolli .................... A61K 9/0019 |
| 2005/0142139 A1 | 6/2005 | Schulke et al. |
| 2007/0122402 A1 | 5/2007 | Bolli et al. |
| 2013/0017191 A1 | 1/2013 | Maeder et al. |
| 2013/0102760 A1 | 4/2013 | Bolli et al. |

FOREIGN PATENT DOCUMENTS

| AU | 2004290899 | 3/2010 |
| CA | 2272245 | 5/1998 |
| DE | 2 364 792 | 7/1974 |
| DE | 3 430 320 | 3/1985 |
| DE | 4 118 912 | 7/1992 |
| EP | 0 025 275 | 3/1981 |
| EP | 0 037 078 | 10/1981 |
| EP | 0 187 712 | 7/1986 |
| EP | 0 196 761 | 10/1986 |
| EP | 0 392 717 | 10/1990 |
| EP | 0 437 622 | 7/1991 |
| EP | 0 528 313 | 2/1993 |
| EP | 0 447 585 | 5/1995 |
| EP | 0 702 960 | 3/1996 |
| EP | 0 852 951 | 7/1998 |
| EP | 0 893 450 | 1/1999 |
| EP | 0 911 037 | 4/1999 |
| EP | 1 268 551 | 2/2004 |
| EP | 1 084 147 | 9/2004 |
| EP | 1 532 983 | 5/2005 |
| JP | 2001-503781 | 3/1921 |
| JP | S54-20124 | 2/1979 |
| JP | S56-127321 | 10/1981 |

(Continued)

OTHER PUBLICATIONS

Opponent Grifols, S.A.'s response to Proprietor's Letter, filed Jun. 10, 2014, for European Patent No. 1687028 B1 (Application No. 04818790.0-1412) (20 pages).
Document D24 submitted Jun. 10, 2014, with Opponent's Response to Proprietor's Letter, for European Patent No. 1687028 B1 (Application No. 04818790.0-1412): A.W.P. Vermeer et al., "The Thermal Stability of Immunoglobulin: Unfolding and Aggregation of a Multi-Domain Protein," Biophys. J., 78: 394-404 (2000).
Document D25 submitted Jun. 10, 2014, with Opponent's Response to Proprietor's Letter, for European Patent No. 1687028 B1 (Application No. 04818790.0-1412): W.R. Gombotz et al., "The Stabilization of a Human IgM Monoclonal Antibody with Poly(vinylpyrrolidone)," Pharm. Res., 11(5): 624-632 (1994).
Document D26 submitted Jun. 10, 2014, with Opponent's Response to Proprietor's Letter, for European Patent No. 1687028 B1 (Application No. 04818790.0-1412): Certified priority document EP Patent App. No. 03026539.1, filed Nov. 18, 2003 (27 pages).
"2.2.2. Degree of Coloration of Liquids," from European Pharmacopoeia 5.0, Supplement 5.5, pp. 24-26, Jul. 2006.
Decision on Appeal, mailed Dec. 9, 2013, for U.S. Appl. No. 10/579,357.

(Continued)

*Primary Examiner* — Yunsoo Kim
(74) *Attorney, Agent, or Firm* — McNeill Baur PLLC

(57) ABSTRACT

The present invention relates to the use of proline for reducing the viscosity of a protein preparation.

24 Claims, No Drawings

(56) References Cited

FOREIGN PATENT DOCUMENTS

| | | |
|---|---|---|
| JP | S57-31623 | 2/1982 |
| JP | S57-128635 | 8/1982 |
| JP | 60-120823 | 6/1985 |
| JP | 61-194035 | 8/1986 |
| JP | H04-346934 | 12/1992 |
| JP | 05-178719 | 7/1993 |
| JP | H06-510031 | 11/1994 |
| JP | H08-99899 | 4/1996 |
| JP | H10-502938 | 3/1998 |
| JP | 2001-519770 | 10/2001 |
| WO | WO 94/29334 | 12/1994 |
| WO | WO 96/07429 | 3/1996 |
| WO | WO 96/15153 | 5/1996 |
| WO | WO 98/05686 | 2/1998 |
| WO | WO 98/28007 | 7/1998 |
| WO | WO 99/64462 | 12/1999 |
| WO | WO 02/080976 | 10/2002 |
| WO | WO 02/096457 A2 | 12/2002 |
| WO | WO 2004/084816 | 10/2004 |
| WO | WO 2005/049078 | 6/2005 |
| WO | WO 2008/039761 | 4/2008 |
| WO | WO 2011/088120 A1 | 7/2011 |
| WO | WO 2011/104315 | 9/2011 |

OTHER PUBLICATIONS

Record of Oral Hearing, mailed Jan. 24, 2014, for U.S. Appl. No. 10/579,357.
Notice of Allowance and Fee(s) Due, dated Dec. 19, 2013, for U.S. Appl. No. 10/579,357.
Rejection Decision, mailed May 8, 2014, for Chinese Patent App. No. 201180010874.X (4 pages), with translation (4 pages).
Communication pursuant to Article 94(3) EPC for EP Patent App. No. 10177786.0 (3 pages).
Summons to attend oral proceedings pursuant to Rule 115(1) EPC, mailed Jun. 13, 2014, for EP Patent No. 1687028 (17 pages).
Supplemental Proprietor's submission filed Apr. 17, 2014, for European Patent No. 1687028 B1 (Application No. 04818790.0-1412) (7 pages).
Australian Patent Examination Report No. 2; Application No. 2011219828 dated Sep. 3, 2014.
Bolli, R. et al., "L-Proline Reduces IgG Dimer Content and Enhances the Stability of Intravenous Immunoglobulin (IVIG) Solutions," Biologicals, 38:150-157, (2010).
"Peptide Storage and Handling Guidelines" GenScript, The Biology CRO, (2010).
A.W.P. Vermeer et al., "The Thermal Stability of Immunoglobulin: Unfolding and Aggregation of a Multi-Domain Protein," Biophys. J., 78: 394-404 (2000); Document D24 submitted Jun. 10, 2014, with Opponent's Response to Proprietor's Letter, for European Patent No. 1687028 B1 (Application No. 04818790.0-1412).
W.R. Gombotz et al., "The Stabilization of a Human IgM Monoclonal Antibody with Poly(vinylpyrrolidone)," Pharm. Res., 11(5): 624-632 (1994); Document D25 submitted Jun. 10, 2014, with Opponent's Response to Proprietor's Letter, for European Patent No. 1687028 B1 (Application No. 04818790.0-1412).
Notice of Allowance and Fee(s) Due, dated Aug. 5, 2014, for U.S. Appl. No. 13/618,757 (7 pages).
Patent Owner's Response to Notice of Opposition submitted Mar. 7, 2014, for European Patent No. 1687028 B1 (Application No. 04818790.0-1412) (30 pages), including transmittal letter of Carpmaels & Ransford, submission list, observations, and main request claims (13 pages).
Document D17 submitted Mar. 7, 2014, with Patent Owner's Response to Notice of Opposition submitted Mar. 7, 2014, for European Patent No. 1687028 B1 (Application No. 04818790.0-1412): International Blood Plasma News Apr. 2010—Privigen (1 page).
Document D18 submitted Mar. 7, 2014, with Patent Owner's Response to Notice of Opposition submitted Mar. 7, 2014, for European Patent No. 1687028 B1 (Application No. 04818790.0-1412): CSL Behring press release of Feb. 24, 2011 (2 pages).
Document D19 submitted Mar. 7, 2014, with Patent Owner's Response to Notice of Opposition submitted Mar. 7, 2014, for European Patent No. 1687028 B1 (Application No. 04818790.0-1412): Letter from EMEA concerning Hizentra (3 pages).
Document D20 submitted Mar. 7, 2014, with Patent Owner's Response to Notice of Opposition submitted Mar. 7, 2014, for European Patent No. 1687028 B1 (Application No. 04818790.0-1412): Letter from US FDA concerning Hizentra (2 pages).
Document D21 submitted Mar. 7, 2014, with Patent Owner's Response to Notice of Opposition submitted Mar. 7, 2014, for European Patent No. 1687028 B1 (Application No. 04818790.0-1412): Transmittal of Labels and Circulars Mar. 28-29, 2010 from US FDA concerning Privigen (1 page).
Document D22 submitted with Patent Owner's Response to Notice of Opposition submitted Mar. 7, 2014, for European Patent No. 1687028 B1 (Application No. 04818790.0-1412) : Declaration of Annette Gaida (7 pages).
European Search Report dated Apr. 28, 2004, for European Patent Application No. 03026539.1 (10 pages).
PCT International Search Report and Written Opinion dated May 27, 2005, for International Patent Application No. PCT/EP2004/013022 (15 pages).
Notice of the Reason of Rejection dated Jul. 13, 2010, for Japanese Patent Application No. 2006-540301 (3 pages) with translation (4 pages).
Office Action dated Jan. 4, 2011, for Canadian Patent Application No. 2,545,939 (3 pages).
Extended European Search Report dated May 4, 2012, for European Patent Application No. 10177786.0 (9 pages).Notice of Opposition dated Jun. 28, 2013, for European Patent No. 1687028 (21 pages).
T. Arakawa et al., "The Stabilization of Proteins by Osmolytes," Biophys. J., 47: 411-414, (1985).
T. Arakawa et al., "Protein-Solvent Interactions in Pharmaceutical Formulations," Pharmaceutical Research, 8(3): 285-291 (1991).
W.K. Bleeker et al., "An Animal Model for the Detection of Hypotensive Side Effects of Immunoglobulin Preparations," Vox Sang., 52: 281-290 (1987).
J.F. Carpenter et al., "Cryoprotection of Phosphofructokinase with Organic Solutes: Characterization of Enhanced Protection in the Presence of Divalent Cations," Archives of Biochemistry and Biophysics, 250(2): 505-512 (1986).
K.C. Hazen et al., "Cryoprotection of Antibody by Organic Solutes and Organic Solute/Divalent Cation Mixtures," Archives of Biochemistry and Biophysics, 267(1): 363-371 (1988).
D.A. Parkins et al., "The Formulation of Biopharmaceutical Products," Pharmaceutical Science & Technology Today, 3(4): 129-137 (2000).
D. Samuel et al., "Proline is a Protein Solubilizing Solute," Biochemistry and Molecular Biology International, 41(2): 235-242 (1997).
D. Samuel et al., "Proline Inhibits Aggregation During Protein Refolding," Protein Science, 9: 344-352 (2000).
L.T. Smith "Characterization of a .gamma.-Glutamyl Kinase from *Escherichia coli* That Confers Proline Overproduction and Osmotic Tolerance," Journal of Bacteriology, 164(3): 1088-1093 (1985).
S. Taneja et al., "Increased Thermal Stability of Proteins in the Presence of Amino Acids," Biochem. J., 303: 147-153 (1994).
D.L. Tankersley et al., "Immunoglobulin G Dimer: An Idiotype-Anti-Idiotype Complex," Molecular Immunology, 25(1): 41-48 (1988).
U.S. Department of Health and Human Services, Food and Drug Administration, Center for Drug Evaluation and Research (CDER), Center for Biologics Evaluation and Research (CBER), "Guidance for Industry Q1A(R2) Stability Testing of New Drug Substances and Products, Revision 2," Nov. 2003 (25 pages).
Notification of Transmittal of the International Search Report and the Written Opinion of the International Searching Authority, or the Declaration, for International Patent App. No. PCT/EP2011/052770, dated Jun. 9, 2011 (9 pages).

(56) References Cited

OTHER PUBLICATIONS

Extended European Search Report and European Search Opinion for European Patent App. No. 10 001 996.7, dated Aug. 6, 2010 (5 pages).
J.L. Cleland et al., "The Development of Stable Protein Formulations: A Close Look at Protein Aggregation, Deamidation, and Oxidation," Crit. Rev. Therap. Drug Carrier Systems, 10(4): 307-377 (1993).
P. Qi et al., "Characterization of the Photodegradation of a Human IgG1 Monoclonal Antibody Formulated as a High-concentration Liquid Dosage form," J. Pharm. Sci., 98(9): 3117-3130 (2009).
Non-final Office Action, dated Dec. 26, 2013, for U.S. Appl. No. 13/618,757.
Reply to Office Action, filed Mar. 14, 2014, for U.S. Appl. No. 13/618,757.
Final Office Action, dated May 23, 2014, for U.S. Appl. No. 13/618,757.
R. Bolli et al., "L-Proline reduces IgG dimer content and enhances the stability of intravenous immunoglobulin (IVIG) solutions," Biologicals, 38: 150-157 (2010).
M. Cramer et al., "Stability over 36 months of a new liquid 10% polyclonal immunoglobulin product (IgPro10, Privigen ©) stabilized with L-proline," Vox Sanguinis, 96: 219-225 (2009).
S. Misbah et al., "Subcutaneous immunoglobulin: opportunities and outlook," Clinical and Experimental Immunology, 158 (Suppl. 1): 51-59 (2009).
Notification of Transmittal of the International Search Report and the Written Opinion of the International Searching Authority, or the Declaration, for International Patent App. No. PCT/EP2011/051556, dated Feb. 28, 2011 (15 pages).
Extended European Search Report and European Search Opinion for European Patent App. No. 10 001 164.2, dated Jul. 19, 2010 (10 pages).
U.S. Food and Drug Administration package insert for Hizentra, Immune Globulin Subcutaneous (Human), 20% Liquid, issued Feb. 2010 (26 pages).
U.S. Food and Drug Administration package insert for Privigen™, Immune Globulin Intravenous (Human), 10% Liquid, issued Jul. 2007 (20 pages).
International Blood/Plasma News, "CSL Behring announced that the U.S. FDA has approved a supplemental Biologics License Application (sBLA) that extends the shelf life of its Privigen 10% liquid intravenous immunoglobulin product from 24 months to 36 months," p. 12, Apr. 2010.
D.L. Tankersley, "Dimer Formation in Immunoglobulin Preparations and Speculations on the Mechanism of Action of Intravenous Immune Globulin in Autoimmune Diseases," Immunological Reviews 139: 159-172 (1994).
CSL Behring press release, "CSL Behring Receives FDA Approval to Extend Shelf Life of Hizentra™ from18 months to 24 months," Aug. 18, 2010 (2 pages).
H. Lilie, "Folding of the Fab fragment within the intact antibody," FEBS Lett. 417: 239-242 (1997).
M.O. Spycher et al., "Well-tolerated liquid intravenous immunoglobulin G preparations (IVIG) have a low immunoglobulin G dimer (IgG-dimer) content," J. Autoimmun. 96 (Suppl. 1): 96 (1996).
R. Bolli et al. "IgG-dimer formation in liquid immunoglobulin preparations is inhibited by nicotinamide and other amphiphilic compounds," J. Autoimmun. 96 (Suppl. 1): 96 (1996).
G. Lemm, "Composition and properties of IVIg preparations that affect tolerability and therapeutic efficacy," Neurology 59(Suppl. 6): S28-S32 (2002).
W. Wang, "Instability, stabilization, and formulation of liquid protein pharmaceuticals," Int. J. Pharmaceutics 185: 129-188 (1999).
B. Alberts et al., Molecular Biology of the Cell 3.sub.rd Ed. 1994, cover pages and p. G-12.
A.K. Abbas et al., Cellular and Molecular Immunology 4.sup.th Ed. 2000, cover pages and pp. 470 and 482.

I. Andresen et al., "Product equivalence study comparing the tolerability, pharmacokinetics, and pharmacodynamics of various human immunoglobulin-G formulations," J. Clin Pharmacol, vol. 40, pp. 722-730 (2000).
T.K.S. Kumar et al., "The Role of Proline in the Prevention of Aggregation During Protein Folding In Vitro," Biochem. Mol. Biol. Int., 46(3): 509-517 (1998).
K. Shiraki et al. "Biophysical Effect of Amino Acids on the Prevention of Protein Aggregation," J. Biochem., 132(4): 591-595 (2002).
English Language Derwent abstract of JP 05-178719 A, 1980.
English Language Derwent abstract of JP 60-120823 A, 1985.
English Language Derwent abstract of JP 61-194035 A, 1994.
I. Andersson et al., "An Improved Chromatography Method for Production of IgG from Human Plasma," Presented at XXIII Congress of the International Society of Blood Transfusion (1994).
J.-P. Azulay et al., "Intravenous Immunoglobulin Treatment in Patients With Motor Neuron Syndromes Associated With Anti-GM.sub.1 Antibodies, A Double-Blind, Placebo-Controlled Study," Neurology, 44: 429-432 (1994).
M. Basta et al., "High-Dose Intravenous Immunoglobulin Exerts its Beneficial Effect in Patients with Dermatomyositis by Blocking Endomysial Deposition of Activated Complement Fragments," J. Clin. Invest., 94: 1729-1735 (1994).
S.A. Berkman et al., "Clinical Uses of Intravenous Immunoglobulins," Annals Internal Medicine, 112: 278-292 (1990).
L. Biesert, "Virus Validation Studies of Immunoglobulin Preparations," Clin. Exp. Rheumatol., 14(Suppl. 15): S47-S52 (1996).
J. Bjorkander et al., "1040 Prophylactic Infusions with an Unmodified Intravenous Immunoglobulin Product Causing Few Side-Effects in Patients with Antibody Deficiency Syndromes," Infection, 13(3): 102-110 (1985).
B. Brenner, "Clinical Experience With Octagam, a Solvent Detergent (SD) Virus Inactivated Intravenous Gammaglobulin," Clin. Exp. Rheumatol., 14(Suppl. 15): S115-S119 (1996).
R.H. Buckley et al., "The Use of Intravenous Immune Globulin in Immunodeficiency Diseases," New Eng. J. Med., 325(2): 110-117 (1991).
P. Cassulis et al., "Ligand Affinity Chromatographic Separation of Serum IgG on Recombinant Protein G-Silica," Clin. Chem., 37(6): 882-886 (1991).
M.-F. Clerc et al., "Labelling of Colloidal Gold with IgE," Histochemistry, 89: 343-349 (1988).
Cooperative Group for the Study of Immunoglobulin in Chronic Lymphocytic Leukemia, "Intravenous Immunoglobulin for the Prevention of Infection in Chronic Lymphocytic Leukemia, A Randomized, Controlled Clinical Trial," New Eng. J. Med., 319: 902-907 (1998).
M.C. Dalakas, "Intravenous Immune Globulin Therapy for Neurologic Diseases," Ann. Int. Med., 126(9): 721-730 (1997).
J.M. Dwyer, "Manipulating the Immune System with Immune Globulin," New Eng. J. Med., 326(2): 107-116 (1992).
S. El Alaoui et al., "Development of an Immunocapture Method for Measuring IgA Antibodies to Tissue Transglutaminase in the Sera of Patients with Coeliac Disease," Clin. Exp. Immunol., 144: 101-109 (2006).
Gammagard S/D, "Humanes Immunoglobulin Zur Intravenosen Anwendung Solvent/Detergent Behandelt," Product Information, Baxter Deutschland GmbH, Edisonstr. 3-4, D-85716 Unterschleibheim, Germany (1994).
A.F.S.A. Habeeb et al., "Preparation of Human Immunoglobulin by Caprylic Acid Precipitation," Preparative Biochem., 4(1): 1-17 (1984).
P. Hansen et al., "Isolation and Purification of Immunoglobulins from Chicken Eggs Using Thiophilic Interaction Chromatography," J. Immunol. Meth., 215: 1-7 (1998).
J.R. Harris, Ed., "Blood Separation and Plasma Fractionation," pp. 332-333, Wiley-Liss, New York (1991).
H. Hocini et al., "An ELISA Method to Measure Total and Specific Human Secretory IgA Subclasses Based on Selective Degradation by IgA1-Protease," J. Immunol. Meth., 235(1-2): 53-60 (2000) (Abstract).

(56) References Cited

OTHER PUBLICATIONS

S.-V. Kaveri et al., "Intravenous Immunoglobulins (IVIg) in the Treatment of Autoimmune Diseases," Clin. Exp. Immunol., vol. 86, pp. 192-198 (1991).
W.J. Koopman et al., "A Sensitive Radioimmunoassay for Quantitation of IgM Rheumatoid Factor," Arth. Rheum., 23(3): 302-308 (1980).
J.L. Lundblad et al., "Comparative Studies of Impurities in Intravenous Immunoglobulin Preparations," The University of Chicago, Rev. Infectious Diseases, 8(Supp. 4): S382-S390 (1986).
J.P. McCue, "Changes in Therapeutic Proteins Caused by Preparation Techniques," Ann. Internal Medicine, 111(4): 271-272 (1989).
T.E. Mollnes et al., "Effect of Whole and Fractionated Intravenous Immunoglobulin on Complement In Vitro," Mol. Immunol., 34(10): 719-729 (1997).
N. Nourichafi et al., "Comparison of various chromatographic supports for purifying human plasmatic immunoglobulins from Cohn II+III fraction," Biotech. Blood Proteins, 227: 207-212 (1993).
U.E. Nydegger, "Sepsis and Polyspecific Intravenous Immunoglobulins," J. Clin. Apheresis, 12: 93-99 (1997).
G. Oldham et al., "A Quantitative Method for Measuring in vitro Synthesis of IgA and IgG by Human Rectal Mucosa: Studies on normal controls and patients with hypogammaglobulinaemia," Immunol., 37: 661-668 (1979).
R.K. Scopes, "Protein Purification, Principles and Practice," 2nd Edition, pp. 42-45, in "Springer Advance Texts in Chemistry," Charles R. Cantor Ed., Springer-Verlag, N.Y. (1987).
M. Stucki et. al., "Characterisation of a Chromatographically Produced Anti-D Immunoglobulin Product," J. Chromatograph B., 700: 241-248 (1997).
F.B. Waldo et al., "Mixed IgA—IgG Aggregates as a Model of Immune Complexes in IgA Nephropathy," J. Immunol., 142(11): 3841-3846 (1989).
W. Wang, "Antibody Structure, Instability, and Formulation," J. Pharm. Sci., 96(1): 1-26 (2007).
J.V. Wells et al., "Cord Serum IgA Levels in Australian Infants," J. Paediatrics Child Health, 16(3): 189-90 (1980) (Abstract).
English Language Derwent abstract of DE 2 364 792, 1980.
English Language Derwent abstract of DE 3 430 320 A1, 1985.
English Language Derwent abstract of DE 4 118 912 C1, 1992.
Restriction Requirement dated May 12, 2008, for U.S. Appl. No. 10/579,357.
Response to Restriction Requirement, filed Jun. 12, 2008, for U.S. Appl. No. 10/579,357.
Office Action, dated Sep. 26, 2008, for U.S. Appl. No. 10/579,357.
Response to Office Action, filed Feb. 9, 2009, for U.S. Appl. No. 10/579,357.
Final Office Action, dated May 5, 2009, for U.S. Appl. No. 10/579,357.
Amendment and Response under 37 C.F.R § 1.116, filed Aug. 4, 2009, for U.S. Appl. No. 10/579,357.
Advisory Action, dated Aug. 7, 2009, for U.S. Appl. No. 10/579,357.
Request for Continued Examination, filed Sep. 3, 2009, for U.S. Appl. No. 10/579,357.
Office Action, dated Nov. 16, 2009, for U.S. Appl. No. 10/579,357.
Reply to Office Action, filed Feb. 16, 2010, for U.S. Appl. No. 10/579,357.
Final Office Action, dated May 19, 2010, for U.S. Appl. No. 10/579,357.
Interview Summary, dated Aug. 19, 2010, for U.S. Appl. No. 10/579,357.
Request for Continued Examination and Reply to Office Action under 37 C.F.R. § 1.114, filed Sep. 17, 2010, for U.S. Appl. No. 10/579,357.
Office Action, dated Jun. 7, 2010, for U.S. Appl. No. 10/579,357.
Notice of Appeal under 37 C.F.R. § 41.31, filed Sep. 7, 2011, for U.S. Appl. No. 10/579,357.
Appeal Brief under Board Rule § 41.37, filed Oct. 3, 2011, for U.S. Appl. No. 10/579,357.
Examiner's Answer, dated Dec. 21, 2011, for U.S. Appl. No. 10/579,357.
Reply Brief under Board Rule § 41.41 and Request for Oral Hearing, filed Feb. 21, 2012, for U.S. Appl. No. 10/579,357.
V. Burckbuchler et al., Rheological and syringeability properties of highly concentrated human polyclonal immunoglobulin solutions, Eur. J. Pharm. Biopharm., 76: 351-356 (2010).

* cited by examiner

PROCESS FOR PREPARING AN IMMUNOGLOBULIN PREPARATION

This application is a continuation of U.S. application Ser. No. 13/577,220, filed Aug. 3, 2012, which is the US national stage of International Application No. PCT/EP2011/051556, filed Feb. 3, 2011, which claims priority to European Application No. 10 001 164.2, filed Feb. 4, 2010, all of which are incorporated herein by reference.

The present invention relates to the use of proline, and in particular L-proline, to reduce the viscosity of a protein preparation, preferably of an immunoglobulin (Ig) preparation, more preferably of an Ig preparation comprising Ig in a mass-volume percentage of at least 18%.

The present invention further relates to a process for preparing an Ig preparation comprising Ig in a mass-volume percentage of at least 18%, to an Ig preparation obtainable by said process and to the use of said Ig preparation for preparing a medicament for the subcutaneous administration to a human.

Primary immunodeficiency (PID) disorders, such as common variable immunodeficiency (CVID) and X-linked agammaglobulinemia, predispose patients to recurrent infections. These patients require immunoglobulin (Ig) replacement therapy, which can be administered intravenously (IVIg) or subcutaneously (SCIg). Immunoglobulin therapy with IVIg or SCIg has also been shown to be useful in the treatment of other conditions, for example in the treatment of inflammatory and autoimmune conditions, as well as certain neurological disorders.

If immunoglobulin is administered via the more common intravenous route, a sharp rise in serum immunoglobulin level is produced which declines as Ig redistributes into the extravascular space over the next 48 hours, and then falls with first-order kinetics over approximately three weeks before intravenous administration is repeated. Many patients report feeling a "wear-off"-effect during the last week of the dosing interval, in particular malaise, fatigue, arthralgias, myalgias or increased susceptibility to infections.

Considering the drawbacks of intravenous Ig administration, Ig administration via the subcutaneous route has become increasingly popular in recent years. The method does not require venous access, is associated with only few systemic side effects and has been reported to improve patient's quality of life.

One of the major challenges in the formulation of an Ig preparation, and in particular of an Ig preparation for subcutaneous administration, lies in the fact that Ig dissolved in aqueous solution tend to aggregate and form precipitates if not sufficiently stabilised with appropriate additives. Carbohydrates are sometimes used as stabilisers; however, increasing concentrations of carbohydrates are associated with poor tolerability, in particular in the treatment of patients with impaired kidney function (e.g. diabetes patients).

With regard to the stabilisation of monomeric Ig, particularly good results have been achieved by using a basic or non-polar amino acid as a stabiliser. As for example disclosed in WO 2005/049078, the addition of basic or non-polar amino acids and the adjustment of the pH of the final preparation have been found to markedly decrease the formation of aggregates and thus increase the stability of those preparations, particularly at ambient temperature.

When using the subcutaneous route for Ig-treatment of certain indications, relatively large volumes of Ig preparations need to be administered. With the currently available Ig formulations of up to 16% (160 g/l), the inability of tissues to accept large volumes of infused Ig preparation rapidly presents a limitation to subcutaneous administration. Thus, patients receiving Ig via the subcutaneous route need a relatively frequent administration of relatively small volumes at multiple sites. Some patients and physicians regard the multiple sites and frequent subcutaneous infusions as burdensome enough to decline or recommend against SCIg therapy.

In view of this, Ig preparations having a higher Ig concentration would thus be desirable. However, an increase in the Ig concentration goes along with a non-linear increase in viscosity which rapidly presents a limitation to the subcutaneous administration with conventional means. Specifically, highly viscous Ig preparations develop a high back-pressure and therefore compromise proper infusion by the infusion pump. In particular, a prolonged duration of administration compared to preparations having a lower concentration can be expected. This might consequently lead to a decrease in the acceptance of the subcutaneous route.

Also with regard to the manufacturing process, the handling of a highly viscous Ig preparation is relatively cumbersome.

It is thus an object of the present invention to provide a simple means for reducing the viscosity of a protein preparation, particularly of an Ig preparation and more particularly of an Ig preparation having a high Ig concentration.

It is a further object of the present invention to provide a highly concentrated Ig preparation, which is suitable for subcutaneous administration and which by at least maintaining the efficacy of currently available Ig preparations allows for an administration of smaller volumes in a fast and simple manner.

The problem is solved by the subject matter according to the independent claims. Preferred embodiments are defined in the dependent claims.

According to a first aspect, the present invention thus relates to the use of proline for reducing the viscosity of a protein preparation, preferably of an Ig preparation.

The term "viscosity" as used in the context of the present invention means dynamic viscosity. The SI physical unit of dynamic viscosity is millipascal second (mPa·s).

The viscosity can for example be determined by a falling ball viscosimeter ("Kugelfallviskosimeter") according to Höppler in accordance with the European Pharmacopoeia Version 6.0 at 2.2.49 and the requirements of DIN 53015. Thereby, the rolling time of a ball or sphere in a tube or capillary of defined dimensions and having a defined slope is determined. Based on the rolling time, the viscosity of the liquid in the tube or capillary can be determined. The values given in the present application text have been determined by the above principle using a microviscosimeter of the type AMV200 (of Anton Paar GmbH, Graz, Austria). The measurements have been made at a temperature of 20.0° C.+/− 0.1° C.

It has surprisingly been found by the present inventors that by adding proline, and in particular L-proline, a relatively low viscosity of the Ig preparation can be achieved even if the concentration of Ig is high. The same effect can be achieved for other protein preparations, for example for an albumin preparation.

Proline has been reported to have a stabilising effect on protein preparations, its effect of reducing the viscosity of a protein preparation, and in particular of an Ig preparation, has however nowhere been considered so far.

The presence of proline thus has the double beneficial effect of stabilising Ig on the one hand, and thus allowing to obtain a preparation having a very high stability over a relatively long period of time, and of providing a low viscosity on the other hand, thus allowing administration of the preparation in a fast and simple manner.

As mentioned, the effect of reducing the viscosity is of particular relevance for Ig preparations having a high Ig concentration, specifically Ig preparations having a mass-volume percentage of at least 15%.

In a preferred embodiment, the Ig comprised in the Ig preparation to which the present invention relates essentially consists of IgG. In other preferred embodiments of the invention, the Ig comprised in the Ig preparation essentially consists of IgA or essentially consists of IgM.

In the sense of the present invention, a mass-volume percentage of 15% means 150 g per liter.

According to a second aspect, the present invention also relates to a process for preparing an immunoglobulin preparation comprising immunoglobulin in a mass-volume percentage of at least 18%, wherein said process comprises the step of adding proline to reduce the viscosity of the preparation.

Thus, an Ig preparation having a high Ig concentration and having at the same time a relatively low viscosity can be obtained in a very simple and straightforward manner.

According to a particularly preferred embodiment of the process of the present invention, proline is added at a mass-volume percentage of the immunoglobulin of less than 15%, preferably less than 14%, more preferably less than 13%, and most preferably less than 12%, before concentrating the preparation to the mass-volume percentage of the immunoglobulin of at least 18%.

In contrast to the conventional process for the formulation of Ig preparations, the stabiliser—in this case proline—is added before the final concentration step. Thus, the protein in the concentrated product is less subject to stress conditions (e.g. shear forces) as it would be the case if the stabiliser is added after the concentrating step. The process according to this embodiment thus allows for a very gentle treatment of the product.

As set forth above, proline used in the process of the present invention is preferably L-proline.

According to a further preferred embodiment of the process of the present invention, the amount of proline added is such that the concentration of proline in the immunoglobulin preparation ranges from about 10 to about 1000 mmol/l, more preferably from about 100 to about 500 mmol/l, and most preferably is about 250 mmol/l.

According to a particularly preferred embodiment of the process, an Ig preparation comprising Ig in a mass-volume percentage ranging from 18% to less than 20% is prepared, whereby proline is added in an amount such that the viscosity is less than 13 mPa·s, preferably less than 11 mPa·s, more preferably less than 10 mPa·s, and most preferably less than 9 mPa·s.

According to an alternative particularly preferred embodiment, an Ig preparation comprising Ig in a mass-volume percentage of at least 20% is prepared, wherein proline is added in an amount such that the viscosity is less than 19 mPa·s, preferably less than 17 mPa·s, more preferably less than 15 mPa·s, and most preferably less than 13 mPa·s.

Having learned from the teaching of the present invention, a skilled person readily realizes how to choose the respective amounts of proline in order to achieve the viscosity aimed for.

According to a third aspect, the present invention relates to an Ig preparation obtainable by the above process.

In particular, the present invention thus relates to an Ig preparation comprising Ig in a mass-volume percentage ranging from 18% to 20%, wherein said preparation comprises proline in an amount such that the viscosity is less than 13 mPa·s, preferably less than 11 mPa·s, more preferably less than 10 mPa·s, and most preferably less than 9 mPa·s.

More particularly, the present invention relates to an Ig preparation comprising Ig in a mass-volume percentage of 18% to 19%, wherein said preparation comprises proline in an amount such that the viscosity is less than 12 mPa·s, preferably less than 11 mPa·s, and to an Ig preparation comprising Ig in a mass-volume percentage of more than 19% to less than 20%, wherein said preparation comprises proline in an amount such that the viscosity is less than 15 mPa·s, preferably less than 13 mPa·s.

Alternatively, the present invention also relates to an Ig preparation comprising Ig in a mass-volume percentage of at least 20%, wherein said preparation comprises proline in an amount such that the viscosity is less than 19 mPa·s, preferably less than 17 mPa·s, more preferably less than 15 mPa·s, and most preferably less than 13 mPa·s.

More particularly, the present invention relates to an Ig preparation comprising Ig in a mass-volume percentage of more than 20% and at the most 22%, wherein said preparation comprises proline in an amount such that the viscosity is less than 19 mPa·s, preferably less than 17 mPa·s, more preferably less than 14 mPa·s, most preferably less than 12 mPa·s, and to an Ig preparation comprising Ig in a mass-volume percentage of more than 22%, wherein said preparation comprises proline in an amount such that the viscosity is less than 27 mPa·s, more preferably less than 20 mPa·s.

Apart from the Ig preparations defined above, the following Ig preparations can be achieved by using proline according to the present invention:

an Ig preparation comprising Ig in a mass-volume percentage of more than 16% and at the most 17%, wherein said preparation comprises proline in an amount such that the viscosity is less than 8 mPa·s, preferably less than 7 mPa·s, more preferably less than 6 mPa·s; and an Ig preparation comprising Ig in a mass-volume percentage of more than 17% and less than 18%, wherein said preparation comprises proline in an amount such that the viscosity is less than 10 mPa·s, preferably less than 9 mPa·s, more preferably less than 8 mPa·s.

For the purpose described above, highly concentrated Ig preparations, in particular Ig preparations comprising Ig in a mass-volume percentage of about 20%, are particularly preferred.

Such highly concentrated Ig preparations are preferably used for the subcutaneous administration to patients, by way of a non-limiting example for the treatment of PID or CVID. Preferably, the Ig comprised in the Ig preparation of the present invention essentially consists of IgG, as mentioned above, but is in no way limited thereto. In other preferred embodiments of the preparation of the present invention, the Ig comprised essentially consists of IgA or essentially consists of IgM.

Given the high concentration of Ig, the present invention allows smaller volumes of the preparation to be administered to the patient, while maintaining the efficacy compared to conventionally available preparations having a lower Ig concentration.

Despite of its relatively high Ig concentration, the present invention allows the preparation to be administered in a fast and simple manner due to its low viscosity. In particular, conventional means currently used for the conventional Ig preparations of lower concentration can be used for the subcutaneous administration.

Given its low viscosity, the Ig preparation of the present invention allows, for example, administration by direct manual push from a syringe. The possibility to use simple devices, such as a conventional syringe, increases the acceptance of the subcutaneous administration and ultimately lowers the cost of the treatment regimen.

Apart from its very low viscosity, the Ig preparation of the present invention has very high storage stability of at least 24 months when stored at room temperature. The room temperature stability provides improved flexibility and convenience of administration for patients with e.g. PID or CVID, compared with other preparations that must be kept refrigerated.

As set forth above, proline is preferably L-proline. L-proline is normally present in the human body and has a very favourable toxicity profile. The safety of L-proline was investigated in repeated-dose toxicity studies, reproduction toxicity studies, mutagenicity studies and safety pharmacology studies, and no adverse effects were noted.

As also set forth above, the Ig preparation preferably comprises proline, and in particular L-proline in a concentration ranging from about 10 to about 1000 mmol, preferably from about 10 to about 500 mmol/l, more preferably from about 100 to about 500 mmol/l, and most preferably is about 250 mmol/l. L-proline used in this concentration range is rapidly cleared after administration of the preparation without any accumulation.

As sufficient stabilisation is achieved by the presence of proline, and in particular L-proline, the addition of carbohydrates as stabilisers can be avoided. According to a preferred embodiment of the present invention, the preparation is thus essentially free of carbohydrates, which may have a beneficial effect on tolerability.

According to a further preferred embodiment, the Ig preparation has a pH of 4.2 to 5.4, preferably 4.6 to 5.0, most preferably about 4.8, which further contributes to the high stability of the preparation.

As already stated above, an aspect of the invention is the use of a single agent for reducing the viscosity and increasing the stability of an immunoglobulin preparation, wherein the single agent is proline, preferably L-proline. Preferably, the amount of proline added is such that the concentration of proline in the immunoglobulin preparation ranges from 10 to 1000 mmol/l, more preferably from 10 to 500 mmol/l, even more preferably from 100 to 500 mmol/l, most preferably about 250 mmol/l.

Preferably, the immunoglobulin preparation comprises immunoglobulin in a mass-volume percentage of at least 18%, more preferably at least 19%, most preferably at least 20%. Preferably, the immunoglobulin of the immunoglobulin preparation is essentially pure IgG. Alternatively, the immunoglobulin of the immunoglobulin preparation is essentially pure IgA or essentially pure IgM.

As given above, the advantages of the present invention are particularly apparent if the Ig preparation is used for subcutaneous administration to a human. The present invention thus also relates to the use of the Ig preparation for the preparation of a medicament for subcutaneous administration to a human. As for example reported by S. Misbah et al, Clinical and Experimental Immunology, 158 (Suppl. 1); pp. 51-59, there are various advantages of the subcutaneous administration of the preparation over the intravenous administration. In particular, venous access is not required and the need for premedication with corticosteroids and anti-histamines is reduced.

Also, when using the subcutaneous route the marked peaks typically seen with monthly IVIg infusions are damped and persistently elevated Ig levels are obtained leading to a reduction in systemic side effects.

Due to the low viscosity of the Ig preparation of the present invention, administration can be performed in a very fast and simple manner, in particular by direct manual push from a syringe, as mentioned above. Thus, the present invention allows self-administration of the Ig preparation by many patients at home, ultimately resulting in better convenience, better quality of life and fewer absences from work.

In particular, the present invention allows the preparation to be administered by the so-called "rapid push" technique described in the above-mentioned review article of S. Misbah et al. in the context of an Ig preparation of lower concentration (Vivaglobin® comprising Ig in a mass-volume percentage of 16%). According to said technique, a syringe and a 23-25-gauge butterfly needle is used to push SCIg under the skin as fast as the patient is comfortable with (usually 1 to 2 cc/min). Administration by said technique thus usually takes only between 5 and 20 minutes.

A specific, non-limiting example of a process for preparing an IgG preparation of the present invention is given in the following:

EXAMPLE

Process for Preparing IgG Preparation
1. Plasma Pool

Igs were isolated from pooled human plasma derived from numerous (>1000) donors.

Starting from this suspension, the following steps were taken:

a) precipitating the human plasma using ethanol to obtain a precipitate and a supernatant;
b) subjecting the re-suspended precipitate obtained under a) to octanoic acid fractionation followed by filtration and diafiltration;
c) incubating the filtrate obtained under b) at a pH of about 4, followed by filtration;
d) subjecting the filtrate obtained under c) to anion exchange chromatography to obtain an eluate comprising Ig, said Ig comprising IgG in a purity of more than 96%;
e) subjecting the eluate obtained under d) to nanofiltration to obtain a filtrate which is essentially virus free;
f) subjecting the filtrate obtained under e) to diafiltration and ultrafiltration to obtain a filtrate having a mass-volume percentage of IgG of about 12%;
g) adding proline, and in particular L-proline, to the filtrate obtained under f);
h) concentrating the filtrate comprising proline to obtain an IgG preparation having a mass-volume concentration of IgG of about 20%; and
i) adding polysorbate 80 to the IgG preparation.

The constituents and their respective amount in the final preparation are given in Table 1. Also given are the values of selected physicochemical parameters as well as the purity of the final Ig preparation.

TABLE 1

| Composition | |
| --- | --- |
| Constituent | Target Value |
| Protein | 200 g/L |
| L-Proline* | 250 mmol/L (28.8 g/L) |
| Polysorbate 80* | Traces |
| Sodium | ≤10 mmol/L |

| Physicochemical properties | |
| --- | --- |
| Parameter | Target Value |
| Osmolality | ~380 mOsmol/kg bw |
| pH** | 4.8 (measured at 1% protein concentration in NaCl 0.9%) |
| Viscosity | 14.71 mPa · s# |

| Purity | |
| --- | --- |
| Protein | Typical value |
| IgG | >98% |
| IgA | <50 mg/L |
| Monomers + dimers | ≥90.0% |

*L-proline and polysorbate 80 used are of non-animal origin in order to minimise the risk of contaminating the product with transmissible spongiform encephalopathy pathogens.
**To attain the optimum measurement, pH is determined in a water-diluted solution (1% protein [10 g/L] as standard).
Mean value from 28 lots. Viscosity measured at room temperature Further, the viscosity of numerous IgG preparations according to the present invention (comprising L-proline in a concentration of 250 mmol+/−40 mmol/l) has been determined, said preparations differing in the specific mass-volume percentage of IgG. Some measurements with lower proline concentrations (10 to 100 mmol/l) have also been included. The viscosity has been determined by a falling sphere viscosimeter ("Kugelfallviskosimeter") according to Höppler in accordance with the European Pharmacopoeia Version 6.0 at 2.2.49 and the requirements of DIN 53015. In particular, a microviscosimeter of the type AMV200 (of Anton Paar GmbH, Graz, Austria) has been used. The measurements have been made at a temperature of 20.0° C.+/−0.1° C.

The respective results are listed in Table 2:

TABLE 2

| Mass concentration of IgG (g/l) | Viscosity of preparation (mPa · s) | Proline concentration (mmol/l) |
| --- | --- | --- |
| 97.7 | 3.09 | 250 |
| 147.5 | 6.69 | 250 |
| 173.9 | 7.21 | 250 |
| 177.5 | 8.79 | 250 |
| 178.4 | 7.78 | 250 |
| 193.7 | 11.15 | 250 |
| 198.6 | 11.25 | 250 |
| 199.9 | 11.25 | 250 |
| 215.8 | 16.65 | 250 |
| 219.8 | 16.75 | 250 |
| 222.1 | 16.85 | 250 |
| 150 | 5.7 | 100 |
| 143 | 5.8 | 50 |
| 144 | 6.0 | 10 |

In comparison, the viscosity of numerous Ig preparations devoid of proline has been determined, the results of which being listed in Table 3:

TABLE 3

| Mass concentration of IgG (g/l) | Viscosity of preparation (mPa · s) (without proline) |
| --- | --- |
| 108.6 | 2.69 |
| 146.3 | 3.82 |
| 154.9 | 7.38 |
| 185.9 | 13.9 |
| 194.8 | 16.95 |
| 207.6 | 21.9 |
| 227.8 | 34.45 |

According to Tables 2 and 3, the presence of proline leads to a reduction in viscosity at protein concentrations higher than 15%. At a mass concentration of about 200 g/l (mass-volume percentage of about 20%), the viscosity of the preparation according to the present invention is lower than 12 mPa·s and thus far lower than the viscosity of the preparation devoid of proline.

The invention claimed is:

1. A process for preparing an immunoglobulin preparation, wherein the process comprises adding proline to an initial immunoglobulin preparation comprising less than 15% (m/v) immunoglobulin, and concentrating the initial immunoglobulin preparation to prepare a final immunoglobulin preparation comprising at least 20% (m/v) immunoglobulin, and wherein proline is added to the initial immunoglobulin preparation such that the viscosity of the final immunoglobulin preparation is less than 17 mPa·s as measured by a falling ball viscosimeter at 20.0° C.

2. The process of claim 1, wherein no viscosity-lowering agents or stabilizing agents are added to the initial immunoglobulin preparation other than proline.

3. The process of claim 1, wherein the immunoglobulin of the immunoglobulin preparation consists essentially of IgG obtained from pooled human plasma from at least 1000 donors.

4. The process of claim 1, wherein proline is added to the initial immunoglobulin preparation such that the concentration of proline in the final immunoglobulin preparation is from 100 to 500 mmol/l.

5. The process of claim 4, wherein proline is added to the initial immunoglobulin preparation such that the concentration of proline in the final immunoglobulin preparation is about 250 mmol/l.

6. The process of claim 1, wherein the final immunoglobulin preparation is suitable for subcutaneous administration to patients.

7. The process of claim 6, wherein the final immunoglobulin preparation may be administered by direct manual push from a syringe.

8. The process of claim 1, wherein the final immunoglobulin preparation comprises more than 20% and at the most 22% (m/v) immunoglobulin.

9. A process for preparing an immunoglobulin preparation, wherein the process comprises adding proline to an initial immunoglobulin preparation comprising less than 15% (m/v) immunoglobulin, and concentrating the initial immunoglobulin preparation to prepare a final immunoglobulin preparation comprising more than 19% to less than 20% (m/v) immunoglobulin, and wherein proline is added to the initial immunoglobulin preparation such that the viscosity of the final immunoglobulin preparation is less than 15 mPas as measured by a falling ball viscosimeter at 20.0° C.

10. The process of claim 9, wherein no viscosity-lowering agents or stabilizing agents are added to the initial immunoglobulin preparation other than proline.

11. The process of claim 9, wherein the immunoglobulin of the immunoglobulin preparation consists essentially of IgG obtained from pooled human plasma from at least 1000 donors.

12. The process of claim 9, wherein proline is added to the initial immunoglobulin preparation such that the concentration of proline in the final immunoglobulin preparation is from 100 to 500 mmol/l.

13. The process of claim 12, wherein proline is added to the initial immunoglobulin preparation such that the concentration of proline in the final immunoglobulin preparation is about 250 mmol/l.

14. The process of claim 9, wherein the final immunoglobulin preparation is suitable for subcutaneous administration to patients.

15. The process of claim 14, wherein the final immunoglobulin preparation may be administered by direct manual push from a syringe.

16. The process of claim 9, wherein the final immunoglobulin preparation is less than 13 mPa·s as measured by a falling ball viscosimeter at 20.0° C.

17. A process for preparing an immunoglobulin preparation, wherein the process comprises adding proline to an initial immunoglobulin preparation comprising less than 15% (m/v) immunoglobulin, and concentrating the initial immunoglobulin preparation to prepare a final immunoglobulin preparation comprising more than 20% and at the most 22% (m/v) immunoglobulin, and wherein proline is added to the initial immunoglobulin preparation such that the viscosity of the final immunoglobulin preparation is less than 19 mPa·s as measured by a falling ball viscosimeter at 20.0° C.

18. The process of claim 17, wherein no viscosity-lowering agents or stabilizing agents are added to the initial immunoglobulin preparation other than proline.

19. The process of claim 17, wherein the immunoglobulin consists essentially of IgG obtained from pooled human plasma from at least 1000 donors.

20. The process of claim 17, wherein proline is added to the initial immunoglobulin preparation such that the concentration of proline in the final immunoglobulin preparation is from 100 to 500 mmol/l.

21. The process of claim 20, wherein proline is added to the initial immunoglobulin preparation such that the concentration of proline in the final immunoglobulin preparation is about 250 mmol/l.

22. The process of claim 17, wherein the final immunoglobulin preparation is suitable for subcutaneous administration to patients.

23. The process of claim 22, wherein the final immunoglobulin preparation may be administered by direct manual push from a syringe.

24. The process of claim 17, wherein the final immunoglobulin preparation is less than 14 mPa·s as measured by a falling ball viscosimeter at 20.0° C.

* * * * *